(12) United States Patent
Morgan

(10) Patent No.: US 8,449,629 B2
(45) Date of Patent: May 28, 2013

(54) PRODUCTION OF BIODIESEL FUELS WHICH ARE LOW IN GLYCERIN AND SULFUR

(75) Inventor: William Douglas Morgan, Richmond, CA (US)

(73) Assignee: Endicott Biofuels II, LLC, Houston, TX (US)

( * ) Notice: Subject to any disclaimer, the term of this patent is extended or adjusted under 35 U.S.C. 154(b) by 0 days.

(21) Appl. No.: 13/316,118

(22) Filed: Dec. 9, 2011

(65) Prior Publication Data

US 2012/0093698 A1  Apr. 19, 2012

Related U.S. Application Data

(63) Continuation of application No. 12/047,585, filed on Mar. 13, 2008, now Pat. No. 8,123,822.

(60) Provisional application No. 60/894,724, filed on Mar. 14, 2007, provisional application No. 60/894,726, filed on Mar. 14, 2007, provisional application No. 60/894,730, filed on Mar. 14, 2007.

(51) Int. Cl.
*C10L 1/19* (2006.01)
*B01J 10/00* (2006.01)

(52) U.S. Cl.
USPC ............ 44/388; 422/187; 554/169; 554/170; 554/174

(58) Field of Classification Search
None
See application file for complete search history.

(56) References Cited

U.S. PATENT DOCUMENTS

| | | | |
|---|---|---|---|
| 2,320,844 | A | 6/1943 | Black |
| 2,486,630 | A | 11/1949 | Brown |
| 3,707,361 | A | 12/1972 | Annable |
| 4,193,770 | A | 3/1980 | Chase et al. |
| 4,698,186 | A | 10/1987 | Jeromin et al. |
| 5,308,365 | A | 5/1994 | Kesling, Jr. et al. |
| 5,399,731 | A | 3/1995 | Wimmer |
| 5,536,856 | A | 7/1996 | Harrison et al. |
| 5,578,090 | A | 11/1996 | Bradin |
| 6,045,762 | A | 4/2000 | Chuang et al. |
| 6,174,501 | B1 | 1/2001 | Noureddini |
| 6,299,655 | B1 | 10/2001 | Steckel et al. |
| 6,399,801 | B1 | 6/2002 | Smith et al. |

(Continued)

FOREIGN PATENT DOCUMENTS

| | | |
|---|---|---|
| JP | 06-313188 | 11/1994 |
| WO | 90/08127 | 7/1990 |

(Continued)

OTHER PUBLICATIONS

He, B.B., et al., Experimental Optimization of a continuous-flow reactive distillation rector for biodiesel production, 2005, American Society of Agricultural Engineers, vol. 48, issue 6, pp. 2237-2243.*

(Continued)

*Primary Examiner* — Yate K Cutliff
(74) *Attorney, Agent, or Firm* — King & Spalding LLP

(57) ABSTRACT

The present invention relates to a process and apparatus for the production of carboxylic acid esters and/or biodiesel fuel from feedstocks containing fatty acids, glycerated fatty acids, and glycerin by reactive distillation. Specifically, in one embodiment, the present invention relates to the production of biodiesel fuels having low glycerin, water, and sulfur content on an industrial scale.

20 Claims, 6 Drawing Sheets

U.S. PATENT DOCUMENTS

| | | | |
|---|---|---|---|
| 6,630,430 | B1 | 10/2003 | Anantaneni et al. |
| 6,855,838 | B2 | 2/2005 | Haas et al. |
| 6,965,044 | B1 | 11/2005 | Hammond et al. |
| 7,045,100 | B2 | 5/2006 | Ergun et al. |
| 7,091,367 | B2 | 8/2006 | Moritz et al. |
| 7,635,398 | B2 | 12/2009 | Bertram et al. |
| 7,705,170 | B2 | 4/2010 | Geier et al. |
| 2002/0184814 | A1 | 12/2002 | Manka |
| 2004/0060226 | A1 | 4/2004 | Bongart et al. |
| 2004/0106813 | A1 | 6/2004 | Moritz et al. |
| 2004/0254387 | A1 | 12/2004 | Luxem et al. |
| 2005/0039384 | A1 | 2/2005 | Gormley |
| 2005/0081436 | A1 | 4/2005 | Bertram et al. |
| 2005/0261144 | A1 | 11/2005 | Notari et al. |
| 2006/0016751 | A1 | 1/2006 | Ali et al. |
| 2006/0048443 | A1 | 3/2006 | Filippini et al. |
| 2006/0246563 | A1 | 11/2006 | Eroma et al. |
| 2006/0264681 | A1 | 11/2006 | Obenaus et al. |
| 2006/0293533 | A1 | 12/2006 | Iyer |
| 2007/0033865 | A1 | 2/2007 | Caprotti et al. |
| 2007/0049727 | A1 | 3/2007 | Pollock et al. |
| 2007/0124992 | A1 | 6/2007 | Reaney et al. |
| 2007/0129565 | A1 | 6/2007 | Sutton et al. |
| 2007/0130820 | A1 | 6/2007 | Chatterjee et al. |
| 2007/0137097 | A1 | 6/2007 | Ikura |
| 2007/0142652 | A1 | 6/2007 | Arumughan et al. |
| 2007/0158270 | A1 | 7/2007 | Geier et al. |
| 2007/0238905 | A1 | 10/2007 | Arredondo et al. |
| 2007/0260077 | A1 | 11/2007 | Elliott |
| 2007/0277429 | A1 | 12/2007 | Jackam et al. |
| 2007/0277432 | A1 | 12/2007 | Jackam et al. |
| 2008/0051592 | A1 | 2/2008 | McNeff et al. |
| 2008/0051599 | A1 | 2/2008 | Adami et al. |
| 2008/0071125 | A1 | 3/2008 | Li |
| 2009/0188157 | A1 | 7/2009 | Holloway, Jr. et al. |
| 2010/0047884 | A1 | 2/2010 | De Greyt et al. |
| 2010/0136113 | A1 | 6/2010 | Steer et al. |

FOREIGN PATENT DOCUMENTS

| | | |
|---|---|---|
| WO | 95/25152 | 9/1995 |
| WO | 2004/080942 | 9/2004 |
| WO | 2006/093896 | 9/2006 |
| WO | 2007/050030 | 5/2007 |

OTHER PUBLICATIONS

26 U.S.C. § 40A. Jan. 3, 2006. Downloaded on Sep. 30, 2008 from <<http://uscode.house.gov/uscode-cgi/fastweb. exe?getdoc+uscview+usclass+2465+0++%28%29%20%20>>.

Chongkhong, S. et al., "Biodiesel producton by esterification of palm fatty acid distillate," Biomass and Bioenergy, vol. 31, issue 8, pp. 563-568, Aug. 2007, available online May 7, 2007.

Dasari, M. A., "Catalytic Conversion of Glycerol and Sugar Alcohols to Value-Added Products." PhD Thesis. University of Missouri-Columbia. May 2006. Downloaded from <<edt.missouri/Winter2006/Dissertation/DasariM-051506-D4163/research.pdf>>.

Environmental Protection Agency, "Regulation of Fuels and Fuel Additives: Renewable Fuel Standard Program: 40 CFR Part 80" Federal Register, vol. 72, No. 83, pp. 23900-24014, May 1, 2007.

Lotero et al., "The Catalysis of Biodiesel Synthesis," Catalysis, vol. 19, pp. 41-83, 2006.

Ma et al., "Biodiesel Production: a review" Bioresource Technology, vol. 70, pp. 1-15, Oct. 1999.

Japan Takahiro, K. et al., Application No. H6-313188, Nov. 8, 1994, English translation 8 pages.

Japan Takahiro, K. et al., Application No. H6-313188, Nov. 8, 1994, English translation of document 4 pages.

National Biodiesel Board, Specification for Biordiesel (B-100)—ASTM D6751-07a, Mar. 2007, 1 page, National Biodiesel Board.

National Biodiesel Board, Specification for Biodiesel (B-100)—ASTM 6751-10, Aug. 1, 2010, 1 page, National Biodiesel Board.

National Biodiesel Board, Specification for Biodiesel ASTM 6751-02, Jan. 10, 2002, 1 page, National Biodiesel Board.

Gerhard Knothe et al., The Biodiesel Handbook, 2005, pp. 1-286, AOCS Press, Champaign, Illinois.

U.S. Appl. No. 12/172,649, filed Jul. 14, 2008, William Morgan.
U.S. Appl. No. 12/048,028, filed Mar. 13, 2008, William Morgan.
U.S. Appl. No. 12/182,991, filed Jul. 30, 2008, William Morgan.
U.S. Appl. No. 12/172,820, filed Jul. 14, 2008, William Morgan.
U.S. Appl. No. 12/172,875, filed Jul. 14, 2008, William Morgan.
U.S. Appl. No. 12/047,585, filed Mar. 13, 2008, William Morgan.

* cited by examiner

PRODUCTION OF BIODIESEL FUELS WHICH ARE LOW IN GLYCERIN AND SULFUR

This application is a continuation of and claims priority under 35 U.S.C. §120 to U.S. patent application Ser. No. 12/047,585, filed Mar. 13, 2008, titled "Production Of Biodiesel Fuels Which Are Low In Glycerin And Sulfur", which claims the benefit of priority to U.S. provisional application 60/894,724, filed Mar. 14, 2007, titled "Production Of Fatty Acid Esters From Glycerin Containing Feedstocks", U.S. provisional application 60/894,726, filed Mar. 14, 2007, titled "Methods of Producing Triol Ethers By Reactive Distillation", and U.S. provisional application 60/894,730, filed Mar. 14, 2007, titled "Production Of Biodiesel Fuels Low In Glycerin And Sulfur". The contents of each of the above-listed applications are incorporated by reference herein in their entirety.

FIELD OF INVENTION

The present invention relates to a process and apparatus for the production of carboxylic acid esters, including biodiesel fuel, from feedstocks containing fatty acids, glycerated fatty acids, and glycerin by reactive distillation. Specifically, in one embodiment, the present invention relates to the production of biodiesel fuels having low glycerin, water and sulfur content.

BACKGROUND

Diesel fuel is a refined petroleum product which is burned in the engines powering most of the world's trains, ships, and large trucks. Petroleum is, of course, a non-renewable resource of finite supply. Acute shortages and dramatic price increases in petroleum and the refined products derived from petroleum have been suffered by industrialized countries during the past quarter-century. Furthermore, diesel engines which run on petroleum based diesel emit relatively high levels of certain pollutants, especially particulates. Accordingly, extensive research effort is now being directed toward replacing some or all petroleum-based diesel fuel with a cleaner-burning fuel derived from a renewable source such as farm crops.

In an effort to partially replace dependence on petroleum based diesel, vegetable oils have been directly added to diesel fuel. These vegetable oils are composed mainly of triglycerides, and often contain small amounts (typically between 1 and 10% by weight) of free fatty acids. Some vegetable oils may also contain small amounts (typically less than a few percent by weight) of mono- and di-glycerides.

Triglycerides are esters of glycerol, $CH_2(OH)CH(OH)CH_2(OH)$, and three fatty acids. Fatty acids are, in turn, aliphatic compounds containing 4 to 24 carbon atoms and having a terminal carboxyl group. Diglycerides are esters of glycerol and two fatty acids, and monoglycerides are esters of glycerol and one fatty acid. Naturally occurring fatty acids, with only minor exceptions, have an even number of carbon atoms and, if any unsaturation is present, the first double bond is generally located between the ninth and tenth carbon atoms. The characteristics of the triglyceride are influenced by the nature of their fatty acid residues.

The production of alkyl esters from glycerides can occur by transesterification. However, transesterification suffers in that the reaction generally requires the addition of an acid or base catalyst which must be first neutralized thereby generating salts and soaps. In addition, while transesterification results in the separation of fatty acid esters from triglycerides, it also results in the production of glycerin, which must then be separated from the fatty acid esters, glycerin, excess alcohol, salts, and soaps. Furthermore, the use of a strong acid, such as sulfuric acid, typically leads to higher sulfur content in the resulting biodiesel as the acid reacts with the double bonds in the fatty acid chains.

In an effort to overcome some of the problems associated with the production of carboxylic acid esters and biodiesel, the present invention employs reactive distillation as a method to assist in the production of biodiesel fuel having low glycerin, water, and sulfur content. Reactive distillation is also useful in producing fatty acid esters from feedstock containing relatively high concentrations of glycerides in the feed to the esterification step. Reactive distillation is a method wherein specific reactions which are affected by an unfavorable equilibrium position of the main reaction, wherein during the reaction one or more substances are continuously removed from the reaction mixture. Sulfur content is reduced by employing reactive distillation over a solid catalyst bed and free glycerin concentration is reduced by employing fat hydrolysis.

SUMMARY

The present invention provides a continuous process for the production of biodiesel fuel low in glycerin, sulfur, and water from fatty acids feedstocks containing relatively high concentrations of glycerides. In one embodiment, the present invention provides a process wherein fat hydrolysis is used to produce a fatty acid stream, mainly free of glycerides, that is reacted with alcohols by reactive distillation over heterogeneous ion exchange resin catalysts to produce biodiesel. In another embodiment, the present invention provides a process wherein a fatty acid stream containing glycerides is reacted with alcohols by reactive distillation over ion exchange resin catalysts to produce fatty acid alkyl esters. It is another object of the present invention to provide a process allowing for enhanced conversion in equilibrium reactions by continuously removing water content with alcohol vapor. In one embodiment, the invention provides a means of eliminating residual contamination of biodiesel with bound or free glycerin.

According to one aspect of the present invention, there is provided a process which allows for a higher content of glycerin in the fatty acid feedstock for preparation of fatty acid esters on an industrial scale. In particular, the invention involves preparing fatty acids by hydrolysis, such that a significant quantity of mono-, di-, and tri-glycerides remain in the feed stock, thereby lowering the cost of hydrolysis. The invention provides for handling the elevated glycerin content during esterification through reactive distillation processes and vapor-liquid and/or liquid-liquid equilibrium stages.

According to one aspect of the present invention, there is provided a continuous process for the production of mainly glycerin- and glyceride-free fatty acids by fat hydrolysis. The fatty acids are then transformed to biodiesel by reaction of a fatty acid component and an alcohol component, in which the fatty acid component and alcohol component are passed in countercurrent relation through an esterification zone maintained under esterification conditions and containing a solid esterification catalyst. In certain embodiments, the esterification catalyst may be selected from particulate ion exchange resins having sulfonic acid groups, carboxylic acid groups or both. The process is characterized in that the esterification zone includes a column reactor provided with a plurality of esterification trays mounted one above another, each adapted to hold a predetermined liquid volume and a charge of solid esterification catalyst. The less volatile component of the fatty acid component and of the alcohol component is supplied in liquid phase to the uppermost section of the reaction column and the more volatile component is supplied as a vapor to a lower portion of the reaction column. Vapor comprising the more volatile component and water from the esterification can be recovered from an upper part of the column reactor, and the biodiesel can be recovered from a lower part of the column reactor.

In another embodiment, there is provided a continuous process for the production of carboxylic acid esters by reaction of a fatty acid component rich in glycerides and of an alcohol component are passed in countercurrent relation through an esterification zone maintained under esterification conditions and containing a solid esterification catalyst. In certain embodiments, the esterification catalyst may be selected from particulate ion exchange resins having sulfonic acid groups, carboxylic acid groups or both. The process is characterized in that the esterification zone includes a column reactor provided with a plurality of esterification trays mounted one above another, each adapted to hold a predetermined liquid volume and a charge of solid esterification catalyst. Means are provided on each esterification tray to allow liquid phase to pass down the column reactor to the next esterification tray, while retaining the solid esterification catalyst. In addition, means are provided to allow vapor to enter that esterification tray from below and agitate the mixture of liquid and solid esterification catalyst. The less volatile component of the fatty acid component and of the alcohol component is supplied in liquid phase to the uppermost section of the reaction column and the more volatile component is supplied as a vapor to a lower portion of the reaction column. Vapor comprising the more volatile component and water from the esterification can be recovered from an upper part of the column reactor, and the carboxylic acid ester can be recovered from a lower part of the column reactor.

In another embodiment, a process for the preparation of either fatty acid methyl esters or biodiesel from a fatty acid feedstock is provided. A methanol vapor feedstream and a fatty acid feedstream are continuously introduced to a reaction vessel. The methanol and fatty acid are catalytically reacted in a reaction zone in the presence of a heterogeneous esterification catalyst within the reaction vessel to produce fatty acid methyl esters and water. The water is removed from the reaction zone with the methanol vapor and is separated from the alcohol, and the fatty acid methyl esters or biodiesel are collected as the product.

In another embodiment, a process for preparing a biodiesel fuel from a triglyceride feedstock, wherein the biodiesel has a low glycerin and sulfur content is provided. The triglyceride feedstock is introduced into a fat splitter to produce a fatty acid-rich feedstream, which is continuously fed to a reaction vessel. Similarly, an alcohol vapor feedstream is introduced to the reaction column. The fatty acid feedstream and alcohol feedstream catalytically react as they pass countercurrently among the equilibrium stages that hold a solid catalyst to produce biodiesel and water. Water is stripped from the reaction vessel along with alcohol vapor due to the action of the equilibrium stages, separated from the alcohol in an additional step and the alcohol is recycled to the reaction vessel. In one embodiment, the catalytic zone includes an ion exchange resin catalyst comprising —$SO_3H$ or —$CO_2H$ functional groups.

In another embodiment, a biodiesel fuel prepared having a water content is less than 0.050% by volume. In another embodiment, the biodiesel fuel has a kinematic viscosity is between 1.9 and 6 $mm^2/s$. In another embodiment, the biodiesel fuel has a sulfur content is less than 500 ppm, preferably less than 15 ppm. In another embodiment, the free glycerin content of the biodiesel fuel is less than 0.020% by weight. In another embodiment, the total glycerin content of the biodiesel is less than 0.240% by weight.

DETAILED DESCRIPTION

Figure 1:
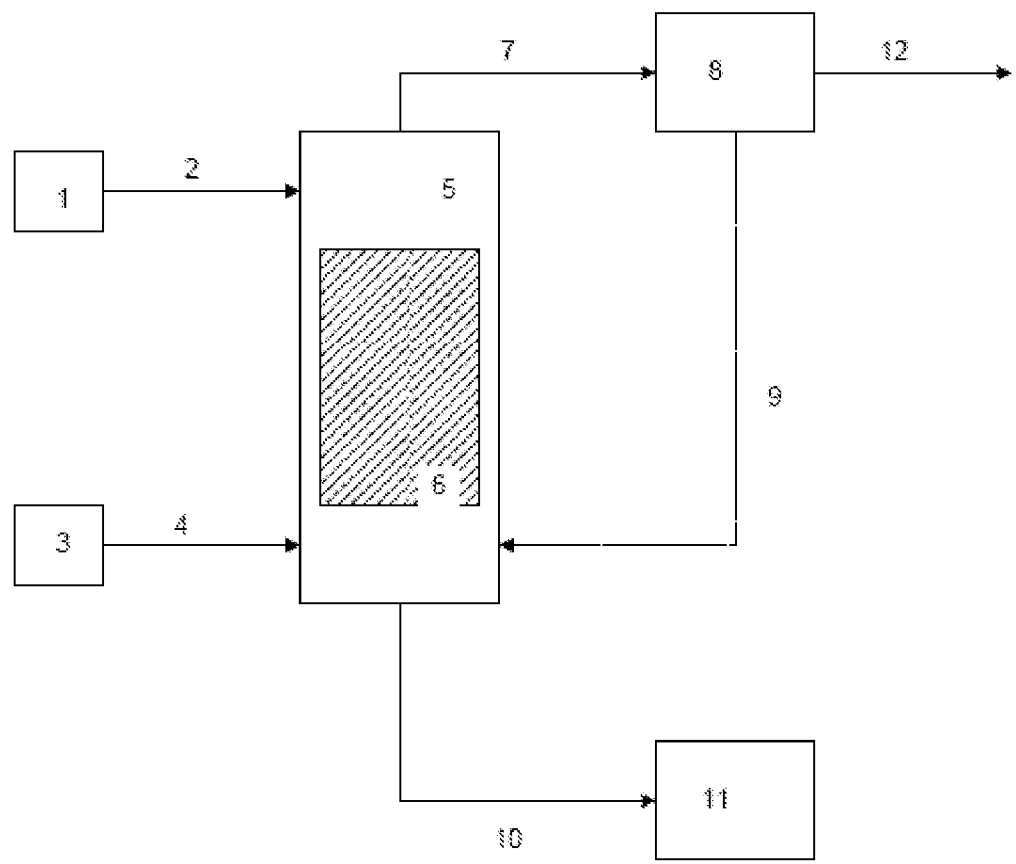
FIG. 1 shows one embodiment of the present reaction for the preparation of fatty acid esters via reactive distillation.

The present invention provides a process for the production of fatty acid esters and/or biodiesel fuels having low glycerin, and optionally low sulfur content, from fatty acids and glycerated fatty acids.

Biodiesel fuels include esters of fatty acids, particularly methyl esters. Generally, the formation of esters from carboxylic acids, for example, proceeds according to the following reaction:

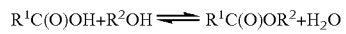

$$R^1C(O)OH + R^2OH \rightleftharpoons R^1C(O)OR^2 + H_2O$$

where $R^1$ is hydrogen or a monovalent organic radical and $R^2$ is a monovalent organic radical. As noted previously, fatty acid esters can also be produced by transesterification whereby glycerides are reacted with alcohols in the presence of acid or base catalysts to yield esters and glycerin. Production of fatty acid esters by transesterification generally produces a product stream having salts and soaps resulting from treatment with acids and/or bases, and a significant concentration of unreacted glycerin. Esterification of fatty acids according to the present invention allows for the inclusion of glycerin in the feedstock without undue consequence to the resulting product. Preferably, the production of fatty acid esters and/or biodiesel fuels according to the invention occurs on an industrial scale. For example, in a preferred embodiment, production occurs from 500 kg or more of feedstock per day. Alternatively, production may occur on batches of 1,000 kg, 5,000 kg, 10,000 kg or more feedstock per day. Global biodiesel production is estimated at several million tons per year.

The process of the present invention employs the vapor stream of the more volatile of the two components, (i.e. the more volatile out of the fatty acid component and the alcohol component), to remove water produced in the esterification reactor, while advantageously not removing a significant quantity of the less volatile component. For this reason it is essential that the boiling point of the vapor mixture exiting the esterification reactor, or of the highest boiling compound present in that vapor mixture, be significantly lower, at the pressure prevailing in the uppermost stage of the esterification reactor, than the boiling point at that pressure of either of the less volatile one of the two components. As used herein with respect to the boiling points, "significantly lower" shall mean that the boiling point difference shall be at least about 20° C., and preferably at least about 25° C., at the relevant operating pressure of the column. In the practice, the more volatile component of the two will frequently be the alcohol component. For example methanol will be the more volatile component in the production from fatty acid mixtures obtained by the hydrolysis of triglycerides of methyl fatty acid ester mixtures for subsequent processing, for example for production of detergent alcohols by ester hydrogenation.

Whereas typical esterification processes employ pure or nearly pure (i.e., 99% or greater) fatty acid feed stocks, the present invention provides a process wherein the feedstock may comprise at least or up to 2% glycerin, at least or up to 3%, at least or up to 4%, at least or up to 5%, at least or up to 6%, at least or up to 7%, at least or up to 8%, at least or up to 9%, or at least or up to 10% glycerin included in the fatty acid feedstock as a result of the splitting of the triglycerides. Ranges and subranges for every amount between 2 and 10% are also envisioned.

Generally, any source of triglycerides can be used to prepare the fatty acid ester derivatives that provides a fuel additive composition with the desired properties. Suitable fatty acids for esterification include, but are not limited to, fatty acids such as decanoic acid, dodecanoic acid, tetradecanoic acid, hexadecanoic acid, octadecanoic acid, octadecenoic acid, linoleic acid, eicosanoic acid, isostearic acid and the like, as well as mixtures of two or more thereof. Mixtures of fatty acids are produced commercially by hydrolysis of naturally occurring triglycerides of vegetable origin, such as coconut oil, rape seed oil, tall oil, and palm oils, and triglycerides of animal origin, such as lard, bacon grease, yellow grease, tallow and fish oils. Additional triglycerides may be sourced from whale oil and poultry fat, as well as corn, palm kernel, soybean, olive, sesame, and any other oils of animal or vegetal origin not explicitly identified herein. If desired, such mixtures of acids can be subjected to distillation to remove lower boiling acids having a lower boiling point than a chosen temperature (e.g. $C_8$ to $C_{10}$ acids) and thus produce a "topped" mixture of acids. Optionally, the mixtures can be distilled to remove higher boiling acids having a boiling point higher than a second chosen temperature (e.g. $C_{22}$+ acids) and thus produce a "tailed" mixture of acids. Additionally, both lower and higher boiling acids may be removed and thus produce a "topped and tailed" mixture of acids. Such fatty acid mixtures may also contain ethylenically unsaturated acids such as oleic acid. These fatty acid mixtures can be esterified with methanol to yield methyl fatty acid ester mixtures.

Naturally-occurring fats and oils are the typically preferred source of triglycerides because of their abundance and renewability. Oils with a higher boiling point are generally preferred over oils with a lower boiling point due to the ease with which such oils may be employed in a reactive distillation process.

Thus, as noted above, the present invention improves fat splitting by allowing for less complete splitting of fat. By reducing the degree of splitting, capacity of fat splitting is increased and cost is decreased.

In another aspect of the present invention, biodiesel fuels prepared according to the present invention are provided. Biodiesels according to international standard EN 14214 or ASTM D 6751 are envisioned.

Sulfur content of the biodiesel fuel is one of many parameters of interest for commercial use. Sulfur is typically present as a result of the use of sulfuric acid catalysts, and can result in increased engine wear and deposits. Additionally, environmental concerns dictate a desired low sulfur content in the biodiesel fuel. Preferably, biodiesels prepared according to the methods provided herein have a sulfur content (as measured by ASTM test method D5453) of less than 3000 ppm, or less than 500 ppm, more preferably less than 200 ppm, less than 100 ppm, less than 50 ppm, less than 25 ppm, less than 10 ppm, and most preferably less than 5 ppm.

It is preferred that biodiesel fuels prepared according to the present method have a relatively high flash point, preferably greater than 130° C., more preferably greater than 140° C., even more preferably greater than 150° C., and most preferably greater than 160° C.

The cetane number (i.e., the measure of the ignition quality of the fuel, as measured by ASTM test methods D976 or D4737) is preferably greater than 47, more preferably greater than 50, and most preferably greater than 55.

Cloud points are defined as the temperature at which a cloud or haze of crystals appears in the fuel. Cloud points determine the climate and season in which the biodiesel fuel may be used. Preferably the cloud point of the biodiesel is less than 0° C., more preferably less than −5° C., less than −10° C., less than −15° C., less than −20° C., less than −25° C., less than −30° C., less than −35° C., less than −40° C., and most preferably, less than −45° C.

Total free glycerin in the biodiesel is preferably less than 0.03% by weight, more preferably less than 0.20% by weight, less than 0.018% by weight, less than 0.016% by weight, and most preferably, less than 0.015% by weight. Total glycerin present in the biodiesel fuel is preferably less than 0.25% by weight, more preferably less than 0.24% by weight, less than 0.23% by weight, less than 0.22% by weight, 0.21% by weight, and most preferably, less than 0.20% by weight.

Residual methanol in the biodiesel is desired to be minimized, and is preferably less than 0.2% by weight, more preferably less than 0.18% by weight, and most preferably less than 0.15% by weight.

Water content in the biodiesel fuel produced according the present invention is preferably less than 500 ppm, preferably less than 450 ppm, more preferably less than 400 ppm and most preferably less than 300 ppm.

It can be important to define a minimum viscosity of the biodiesel fuel because of power loss due to injection pump and injector leakage. Preferably, the viscosity of the biodiesel fuel is between 1.0 and 8.0 mm$^2$/s, more preferably between 1.9 and 6.0 mm$^2$/s, even more preferably between 3.5 and 5.0 mm$^2$/s.

Alcohols

A variety of alcohols may be suitable for use in the present esterification reaction, including any $C_{1-6}$ straight, branched, or cyclic alcohols. Preferably, the alcohol is selected from t-butanol, isobutanol, methanol, ethanol, propanol, isomers of propanol, isomers of butyl and amyl alcohol, isoamyl alcohol, or mixtures thereof. The alcohols employed are preferably anhydrous, however the presence of a small amount of water may be acceptable for the present reaction.

Catalyst

The esterification reaction of the present invention preferably employs a solid heterogeneous catalyst having acidic functional groups on the surface thereof. By heterogeneous is meant that the catalyst is a solid, whereas the reactants are in gaseous and liquid state, respectively.

The solid esterification catalyst may be a granular ion exchange resin containing —SO$_3$H and/or —COOH groups. Macroreticular resins of this type are preferred. Examples of suitable resins are those sold under the trade marks "Amberlyst", "Dowex", "Dow" and "Purolite" such as Amberlyst 13, Amberlyst 66, Dow C351 and Purolite C150.

The catalyst used on each tray or similar vapor liquid equilibrium affecting device can be a single solid esterification catalyst selected from particulate ion exchange resins having acidic groups. A synthetic zeolite or other type of mixed or singular oxide ceramic material with sufficient acidity could also be employed. Furthermore, different trays or stages could contain different catalyst. In other cases, even when a monocarboxylic acid ester is the desired product, the alcohol component and the carboxylic acid component can be reacted to equilibrium in the presence of an acidic ion exchange resin prior to introduction of the resulting equilibrium mixture to the column reactor.

Solid particulate catalyst may also be employed. In this case, the charge of solid particulate or granular esterification catalyst on each tray is typically sufficient to provide a catalyst:liquid ratio on that tray corresponding to a resin concentration of at least 0.2% w/v, for example a resin concentration in the range of from about 2% w/v to about 20% w/v, preferably 5% w/v to 10% w/v, calculated as dry resin. Sufficient catalyst should be used to enable equilibrium or near equilibrium conditions to be established on the tray within the selected residence time at the relevant operating conditions. Additionally, the amount of catalyst on each tray should be maintained such that agitation by the upflowing vapor is sufficient to prevent "dead spots." For a typical resin catalyst a resin concentration in the range of from about 2% v/v to about 20% v/v, preferably 5% v/v to 10% v/v may be used.

Reaction Vessel

The present invention may be practiced in a variety of reaction vessels, preferably in distillation columns having a variety of catalyst arrangements. Preferably, the vessel includes a reaction zone providing means for sufficiently contacting the reactants in the presence of a catalyst. Such means may include a plurality of trays, or structured packing that operates similar to the trays in a column. A suitable distillation column for reactive distillation according to the present invention is described in U.S. Pat. No. 5,536,856 (Harrison, et al.) which is incorporated herein by reference. A different design for the equilibrium stages is described in U.S. Pat. No. 5,831,120 (Watson, et al.), and Sulzer sales brochure ""Katapak: Catalysts and Catalyst Supports with Open Crossflow Structure"; Sulzer Chemtech; (undated)" each of which is incorporated herein by reference. In one embodiment, catalyst can be added and removed from the reaction vessel selectively. For example, when using a plurality of trays, catalyst can be switched from one tray without removing catalyst from other trays.

Exemplary structured packing preferably includes porous catalyst supports and flow channels for the stripping gas between the catalyst supports. In the flow channels, the downward directed flow of the liquid and the upwardly directed stripping gas contact, in the presence of the acidic solid catalyst, so the esterification can take place.

Preferably, the catalyst is macroporous. Additionally, the catalyst selected must have sufficient stability (i.e., minimal loss of activity) at the operating temperatures necessary, depending upon the alcohol component of the reaction. For example, if methanol, ethanol, n-propanol, isopropanol, n-butanol, tert-butanol or isobutanol is selected as the alcohol, then the catalyst (for example, an ion exchange resin), must be able to be used at temperatures between 120° C. and 140° C.; and must only moderately lose activity in this temperature range. If however, 2-ethyl-hexanol is selected as the alcohol component, then the catalyst should be usable at higher temperatures, such as for example, approximately 150° to 230° C.

In certain embodiments, the catalyst can be a fixed-bed catalyst. In a fixed bed arrangement, the reaction vessel can be operated as a trickle column of which about 30 to 60 vol %, preferably about 50 vol % may be utilized by the stripping gas as free gas space, whereas about 30 to 50 vol %, preferably 40 vol % of the column may be occupied by solid substance, i.e. the fixed-bed catalyst. The remaining reaction space, preferably about 10 vol % or less, may be occupied by the trickling liquid. When using a fixed bed, the residence time of the liquid phase can be adjusted by the stripping gas velocity. The residence time of the liquid phase is high with higher velocities of the stripping gas volume. Generally, the stripping gas throughput can be adjusted in a wide range without having an adverse effect on the course of process.

Reaction Conditions

The esterification conditions used in a distillation reactor according to the present invention will normally include the use of elevated temperatures up to about 160° C. Typically, the reaction conditions are determined based upon the boiling point of the less volatile component, typically the alcohol component. Generally, the esterification reaction may be conducted at a temperature in the range of from about 80° C. to about 140° C., preferably in the range of from about 100° C. to about 125° C. The particular operating temperature of the reaction is also determined based on the thermal stability of the esterification catalyst, the kinetics of the reaction and the vapor temperature of the less volatile component at the relevant inlet pressure. Typical operating pressures at the inlet of the column reactor may range from about 0.1 bar to about 25 bar. Additionally, the liquid hourly space velocity through the column reactor may range of from about 0.1 $hr^{-1}$ to about 10 $hr^{-1}$, typically from about 0.2 $hr^{-1}$ to about 2 $hr^{-1}$, may be used. In one embodiment, the ester product remains in the liquid phase while being processed.

Referring now to FIG. 1, there is provided an embodiment of a process for the esterification of fatty acid feed stock having between 1-10% glycerin. A fatty acid feedstock 1 is supplied to column 5 via line 2. If the fatty acid is the less volatile component (compared to the alcohol), then fatty acid 1 is supplied to the upper portion of the column, preferable above a reaction zone 6. An alcohol 3, preferably methanol, is supplied to the column via line 4. If the alcohol is the more volatile component (compared with the fatty acid), then the alcohol 3 is supplied to the bottom of column 5, preferably below the reaction zone 6.

The reaction zone 6 preferably includes trays or structured packing which includes a heterogeneous catalyst, preferably an ion exchange resin having acidic functional groups. If structured packing is employed, preferably achieving the same vapor-liquid contact as is accomplished with trays. One of skill in the art can determine the equivalent size and type of packing for a given number of trays in a distillation column.

The alcohol is introduced at the bottom of the column as a vapor, traveling upward through the trays, and preferably contacting the fatty acid in the reaction zone in the presence of the appropriate esterification catalyst. Column 5 preferably includes means for heating the alcohol to produce a vapor stream. The alcohol stream exits column 5 via line 7, preferably including at least a portion of the water produced by the esterification reaction.

The alcohol stream can be supplied to an alcohol/water separation unit 8, which separates the stream into a water-rich stream 12 and an alcohol rich stream 9, which can be recycled to the distillation column 5.

Product stream 10 exits the distillation column as the bottoms liquid, and includes fatty acid alkyl ethers and glycerin. The bottoms stream 10 may also include mono-, di- and tri-alkyl ethers of glycerin.

Figure 2:
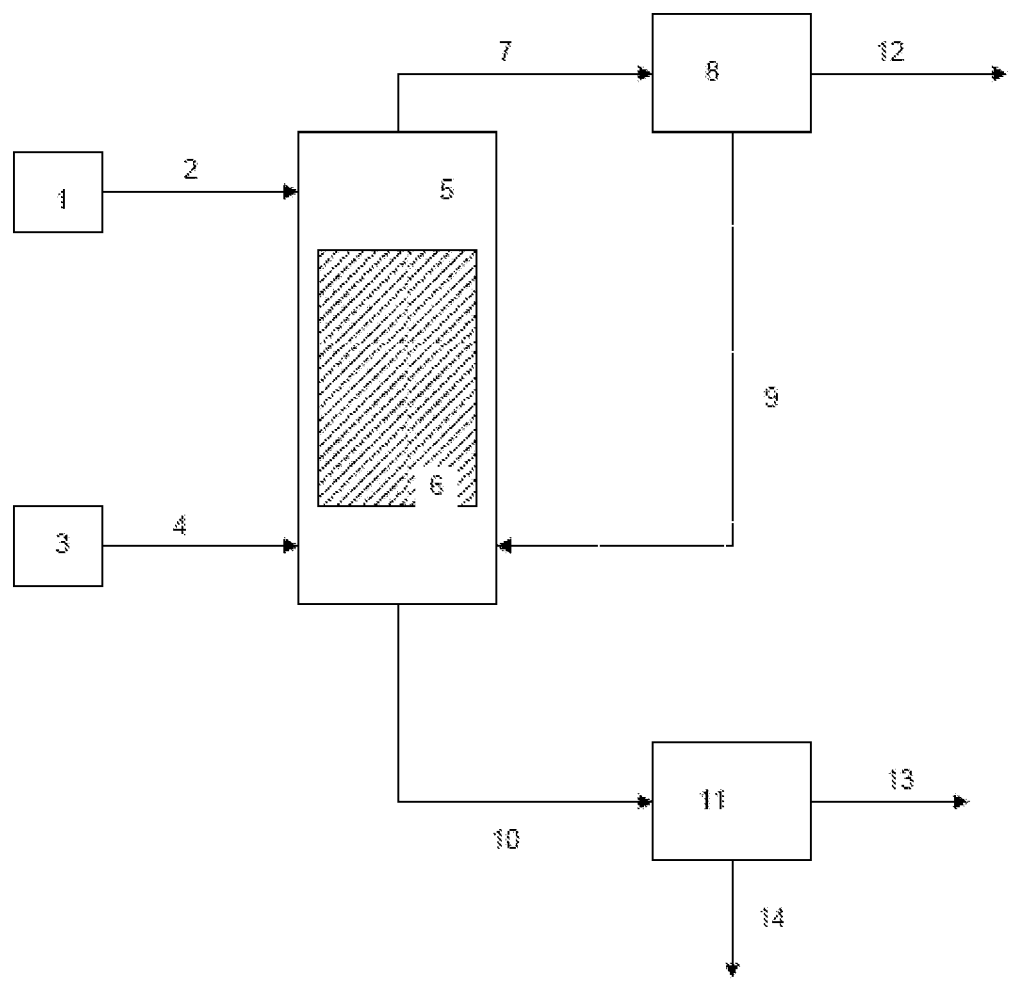
FIG. 2 shows another embodiment of the present invention for the preparation of fatty acid esters, include a separation step for the ester product.

Referring now to FIG. 2, an alternate embodiment of the process shown in FIG. 1 is presented. FIG. 2 shows the process of FIG. 1, and further employs a means for separating 11 the product stream 10. The means can be any means known in the art for the separation of glycerin and unreacted fatty acids from the product esters, such as for example, using a settling tank, distillation, reboiled stripping, inert gas stripping, or physical adsorption. The separation means 11 results in an ester-rich stream 13 and a glycerin or fatty acid containing stream 14.

Figure 3:
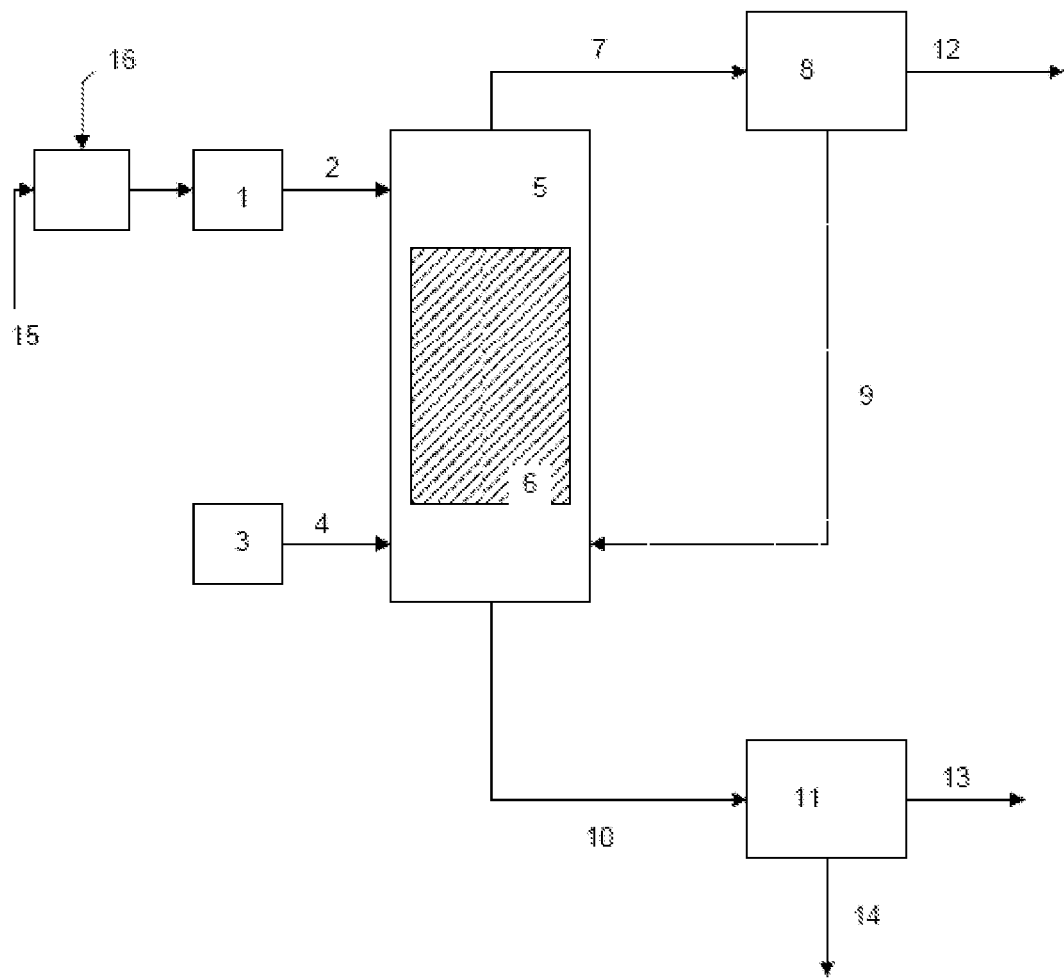
FIG. 3 shows another embodiment of the present invention, further including a pre-esterification process.

Referring to FIG. 3, the embodiment according to FIG. 2 is provided, further including a pre-esterification unit 16, to which the glycerin/fatty acid feed stock is introduced via line 15. The use of a pre-esterification unit may be as is described in U.S. Pat. No. 5,536,856 (Harrison, et al.), incorporated herein by reference.

Figure 4:
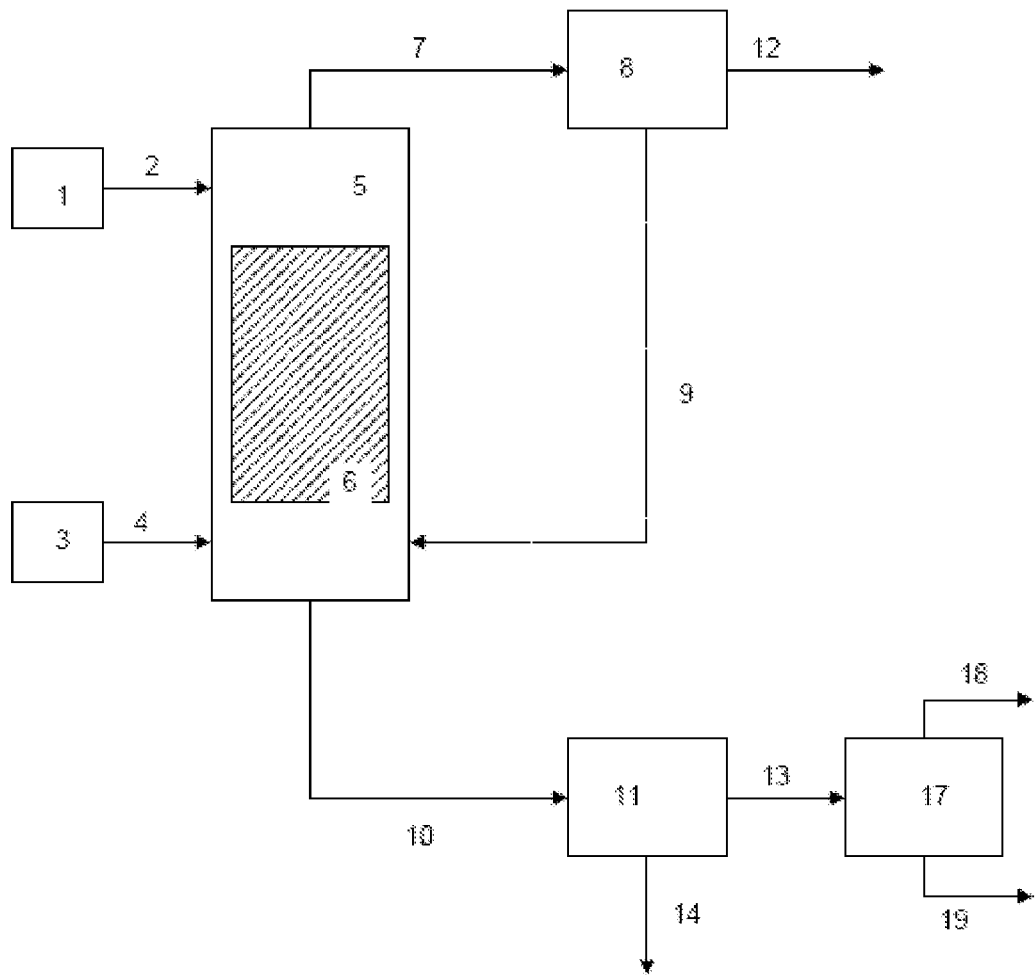
FIG. 4 shows another embodiment of the present invention, further providing a settling tank.

Referring now to FIG. 4, the embodiment according to FIG. 1 is provided, further including means for separating glycerin and the fatty acid ester product of line 13. Accordingly, the product mixture is supplied to a settling tank 17 via line 13. The contents of the tank are allowed to settle, and the fatty acid esters 18 may be separated from the glycerin 19.

Figure 5:
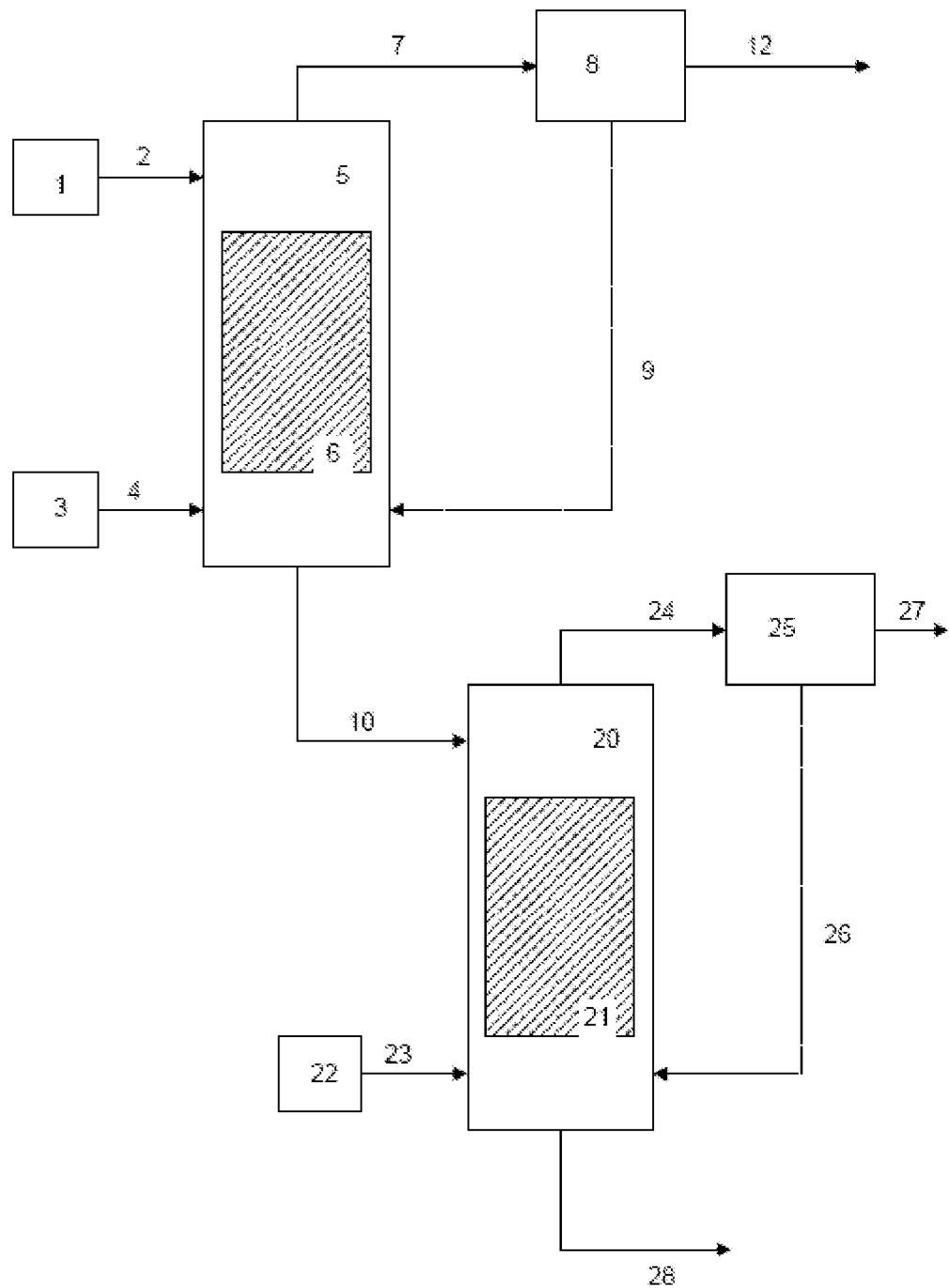
FIG. 5 shows another embodiment of the present invention, further including a reaction vessel for the preparation of a fatty acid ester and ether additive.

Referring now to FIG. 5, an alternate embodiment of the process according to FIG. 1 is provided, further including means for producing a biodiesel feed which includes glycerin ether additives. The glycerin ether additives may be produced by reacting glycerin with an alcohol at a proper temperature and pressure, in the presence of a catalyst, to produce a mixture of mono-, di- and tri-ethers of glycerin.

Crude fatty acid ester product stream 10, which may contain glycerin and unreacted fatty acids, is introduced to a second reaction vessel 20. Reaction vessel 20 is preferably a distillation column configured for reactive distillation. The crude fatty acid ester product stream 10 is introduced into the distillation column above a reaction zone 21. Reaction zone 21 preferably includes trays (equilibrium stages) which include an etherification catalyst. Suitable catalyst for the etherification includes those previously identified as esterification catalysts.

An alcohol 22, preferably tert-butanol, isobutanol or isoamyl alcohol, can be introduced as a vapor to the bottom of reaction vessel 20 via line 23, and functions similar to the alcohol vapor employed in the esterification reactor.

The alcohol vapor 22 reacts with the glycerin from crude feed 10 to produce glycerin ethers. Vaporous alcohol and water resulting from the etherification reaction exit the reactor via line 24, and is introduced to separator 25. Separator 25 may be any known means for separating water from methanol, such as for example, a distillation column. An alcohol rich stream 26 is supplied form separator 25 to the bottom of the etherification reactor 20 as a vapor. Water exits the separator 25 via line 27.

Product stream 28 exits the reaction vessel 20 as a bottoms stream, preferably including the fatty acid ester product of reaction vessel 5 and a glycerin alkyl ether additive.

Figure 6:
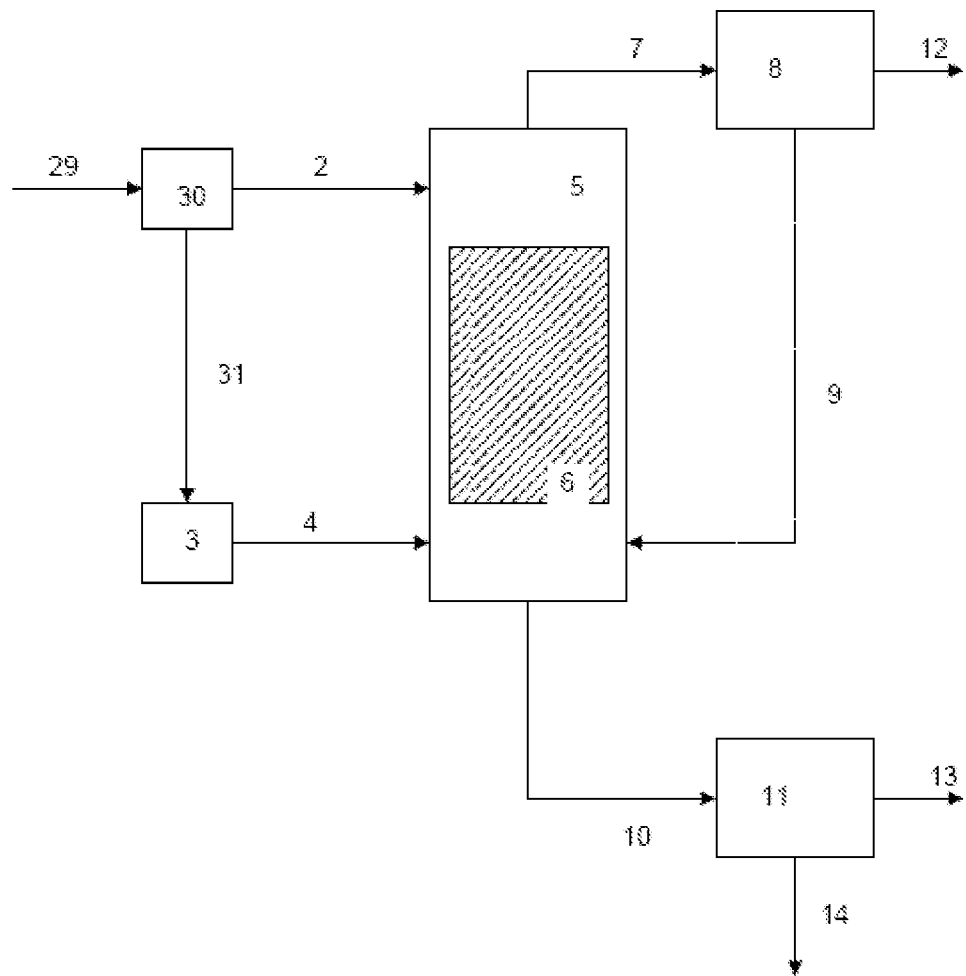
FIG. 6 shows another embodiment of the present invention, further including a fat splitter.

Referring now to FIG. 6, an alternate embodiment for the production of biodiesel fuels is provided. Triglycerides from animal or vegetal oils are supplied via line 29 to a fat splitting unit employing steam to separate triglycerides into component fatty acids and glycerol. The fat splitting unit may be known in the art, as is provided in U.S. Pat. No. 2,486,630 (Brown), incorporated as herein by reference. The majority of the glycerin is separated from the fatty acids, and removed from the fatty acid feedstock via line 31. The fatty acid stream from the fat splitter 30 is supplied to the upper portion of the reactive distillation column, preferable above a reaction zone 6. An alcohol 3, preferably methanol, is supplied to the column via line 4.

The reaction zone 6 preferably includes trays or structured packing which includes a heterogeneous catalyst, preferably an ion exchange resin having acidic functional groups. If structured packing is employed, preferably achieving the same vapor-liquid contact as is accomplished with trays. One of skill in the art can determine the equivalent size and type of packing for a given number of trays in a distillation column.

The alcohol is introduced at the bottom of the column as a vapor, traveling upward through the trays, and preferably contacting the fatty acid in the reaction zone in the presence of the appropriate esterification catalyst. Column 5 preferably includes means for heating the alcohol to produce a vapor stream. The alcohol stream exits column 5 via line 7, preferably including at least a portion of the water produced by the esterification reaction.

The alcohol stream can be supplied to an alcohol/water separation unit 8, which separates the stream into a water-rich stream 12 and an alcohol rich stream 9, which can be recycled to the distillation column 5.

Product stream 10 exits the distillation column as the bottoms liquid, and includes fatty acid alkyl ethers and glycerin. The bottoms stream 10 may also include mono-, di- and tri-alkyl ethers of glycerin.

The product stream 10 is supplied to a separation means 11 to remover impurities from product stream 10. The separation means can be any means known in the art for the separation of glycerin and unreacted fatty acids from the product esters, such as for example, using a settling tank for gravity separation. Optionally, the separation means may also include a filter bed (not shown) which includes bauxite, clay or ion exchange resin beads for further purification. The separation means 11 results in a ester-rich stream 13 and a glycerin or fatty acid containing stream 14.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Modifications and variations of the present invention relating to a the selection of fatty acid feedstocks, alcohols and catalysts may be practiced by those skilled in the art from the foregoing detailed description of the invention. Such modifications and variations are intended to come within the scope of the appended claims.

The invention claimed is:

1. A system for preparing biodiesel from a fatty acid feedstream, the system comprising:
   a reaction vessel comprising an upper section having a fatty acid feedstream introduced thereto, a lower section having an alcohol vapor introduced thereto, and an esterification zone maintained under esterification conditions and comprising a plurality of esterification trays mounted one above the other, each tray having a predetermined liquid volume capacity and charged with a solid heterogeneous ion exchange resin catalyst;

wherein the alcohol vapor and fatty acid feedstream are catalytically esterified in the esterification zone to produce a fatty acid alkyl ester product stream and water;

an alcohol/water separator connected to the reaction vessel, the alcohol/water separator adapted to:

receive unreacted alcohol vapor and the water removed from the upper section by the unreacted alcohol vapor;

separate the unreacted alcohol vapor from the water, and recycle the unreacted alcohol vapor to the lower section of the reaction vessel; and a separation means connected to the reaction vessel and adapted to remove impurities from said fatty acid alkyl ester product stream by at least one process selected from the group consisting of distillation, reboiled stripping, inert gas stripping, physical adsorption, and gravity separation to prepare a biodiesel meeting biodiesel standard ASTM D6751 from the fatty acid alkyl ester product stream.

2. The system of claim 1 further comprising a fat splitter, wherein the fatty acid feedstream is the product of introducing a triglyceride feedstock into the fat splitter to produce a fatty-acid rich feedstream.

3. The system of claim 1, further comprising a pre-esterification unit for pre-esterification of the fatty acid feedstream prior to introduction of the fatty acid feedstream into the reaction vessel.

4. The system of claim 1, wherein the esterification zone includes an ion exchange resin catalyst with —$SO_3H$ or —$CO_2H$ functional groups.

5. The system of claim 1, wherein the catalyst is present in structured packing.

6. The system of claim 1, wherein the catalyst concentration on the trays is at least 0.2% w/v.

7. The system of claim 1, wherein the catalyst concentration on the trays is from about 2% w/v/ to about 20% w/v.

8. The system of claim 1, wherein the alcohol is selected from the group consisting of methanol, ethanol, propanol, isomers of propanol, isomers of butyl and amyl alcohol, isoamyl alcohol, and mixtures thereof.

9. The system of claim 1, wherein the biodiesel comprises a water content of less than 0.050% by volume.

10. The system of claim 1, wherein the biodiesel comprises a kinematic viscosity of between 1.9 and 6 $mm^2/s$.

11. The system of claim 1, wherein the fatty acid alkyl ester product stream comprises fatty acid methyl ester.

12. The system of claim 1, wherein the biodiesel contains from 0 to about 0.25% by weight total glycerin.

13. The system of claim 1, wherein the biodiesel contains from 0 to about 500 ppm sulfur.

14. The system of claim 1, wherein the biodiesel comprises a cetane number greater than 47.

15. The system of claim 1, wherein the biodiesel comprises a total glycerin content of less than 0.20% by weight.

16. The system of claim 1, wherein the biodiesel comprises a cloud point of less than −20° C.

17. The system of claim 1, wherein the biodiesel comprises a cloud point of less than −40° C.

18. The system of claim 1, wherein said fatty acid feedstream comprises one or more fatty acids selected from the group consisting of decanoic acid, dodecanoic acid, tetradecanoic acid, hexadecanoic acid, octadecanoic acid, octadecenoic acid, linoleic acid, eicosanoic acid, and isostearic acid.

19. The system of claim 1, wherein the fatty acid feedstock comprises 99% or greater fatty acids.

20. The system of claim 1, wherein the biodiesel meets EN 14214.

* * * * *